United States Patent [19]

Thurston et al.

[11] Patent Number: 5,429,133
[45] Date of Patent: Jul. 4, 1995

[54] RADIATION RESPONSIVE LAPAROSCOPIC INSTRUMENT

[75] Inventors: Marlin O. Thurston, Columbus; Dale A. Slifko, Westerville, both of Ohio

[73] Assignee: Neoprobe Corporation, Columbus, Ohio

[21] Appl. No.: 992,617

[22] Filed: Dec. 18, 1992

[51] Int. Cl.⁶ .................... A61B 5/00; G01T 1/161
[52] U.S. Cl. .................. 128/653.1; 128/659; 250/336.1; 250/370.01; 250/370.13
[58] Field of Search ............... 128/653.1, 654, 659, 128/5, 6; 250/370.01, 370.07, 370.13, 336.1

[56] References Cited

U.S. PATENT DOCUMENTS

| | | | |
|---|---|---|---|
| 3,669,095 | 6/1972 | Kobayashi et al. | 128/659 |
| 4,243,884 | 1/1981 | Avera, Jr. | 128/659 |
| 4,893,013 | 1/1990 | Denen et al. | 128/659 |
| 4,959,547 | 9/1990 | Carroll et al. | 250/336.1 |
| 4,995,396 | 2/1991 | Inaba et al. | 128/5 |
| 4,996,429 | 2/1991 | Gütner | 250/336.1 |
| 5,036,201 | 7/1991 | Carroll et al. | 250/336.1 |
| 5,215,077 | 6/1993 | Oku | 128/6 |

FOREIGN PATENT DOCUMENTS

| | | | |
|---|---|---|---|
| 2538376 | 3/1976 | Germany | 250/370.13 |
| 2117900 | 10/1983 | United Kingdom | 250/370.13 |

*Primary Examiner*—Krista M. Pfaffle
*Attorney, Agent, or Firm*—Mueller and Smith

[57] ABSTRACT

A laparoscopic instrument is provided having a hand-grippable base to which an elongate accessing tube is connected which extends to a tip. Extending inwardly from the tip is a detection support region within which is formed a radiation transmissive window. Immediately spaced from and behind the window there is positioned a detecting crystal such as cadmium telluride which is retained in a crystal mount structure having an architecture designed for minimizing noise generation occasioned from microphonic (piezoelectric) phenomena and the like.

21 Claims, 8 Drawing Sheets

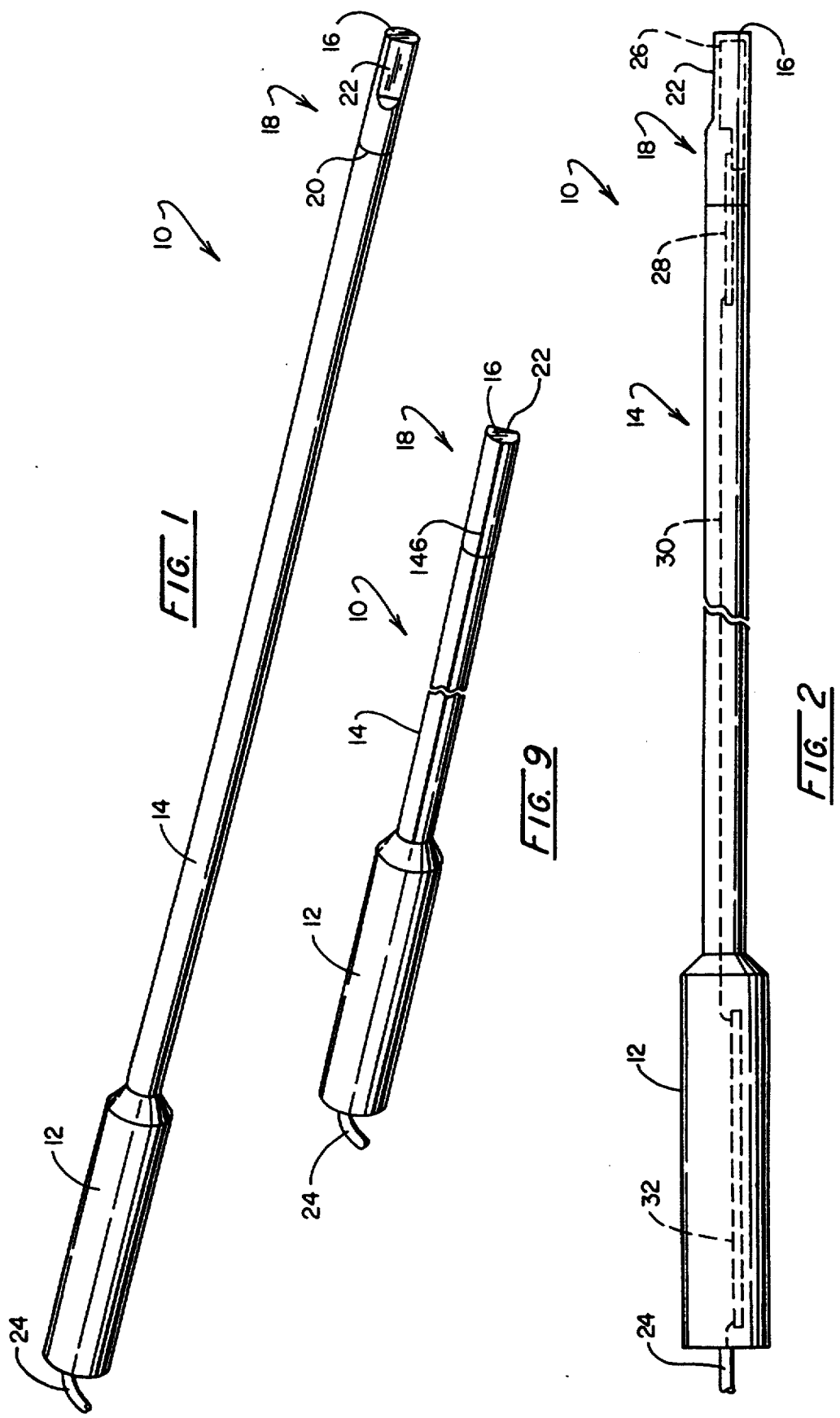

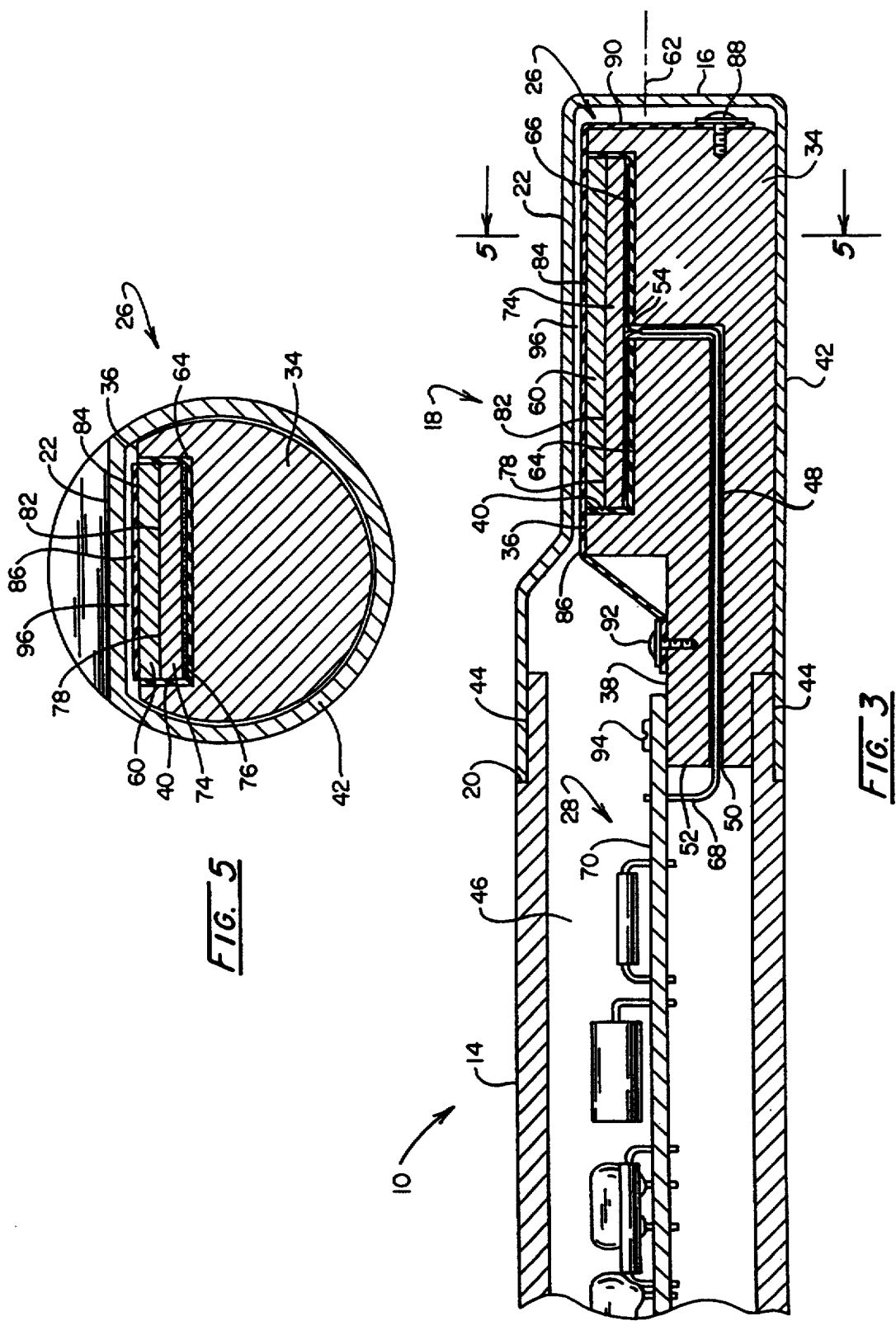

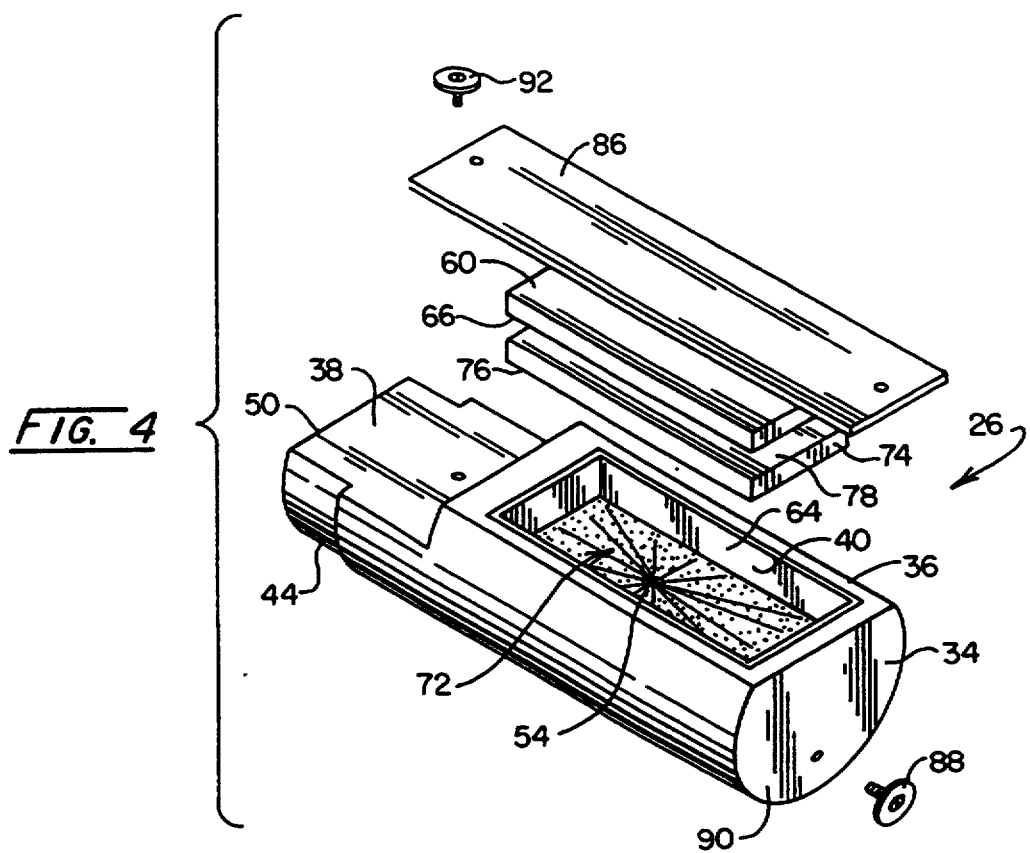
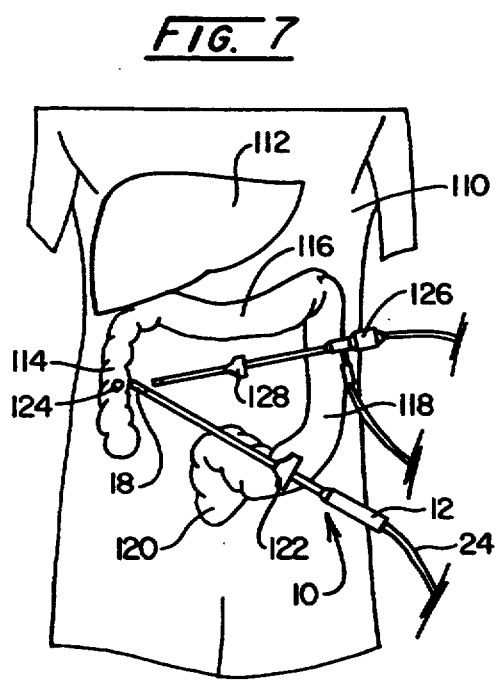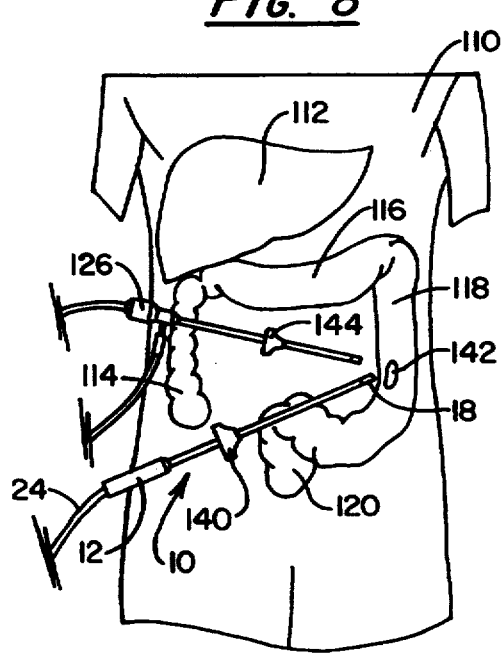

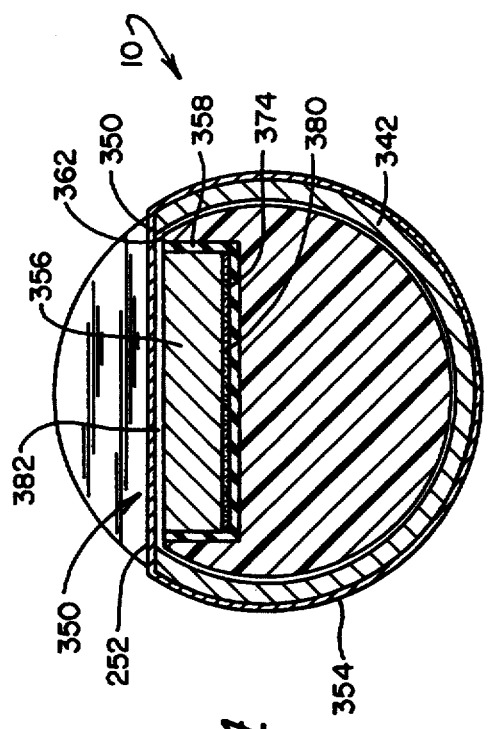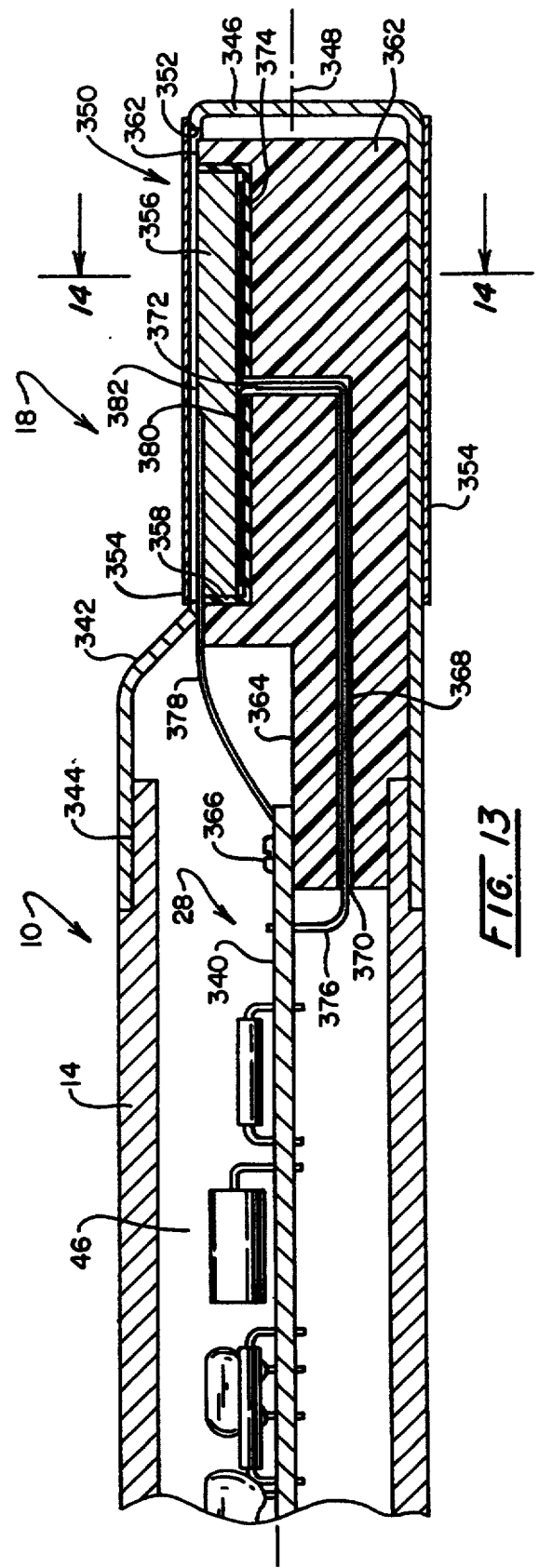

RADIATION RESPONSIVE LAPAROSCOPIC INSTRUMENT

BACKGROUND OF THE INVENTION

Current and historical procedures for the treatment of colon and rectal cancer have been based, for staging purposes, upon the natural history of tumor spread, and thence, upon operative and non-operative options. Operative options generally have looked to the physical location and surgical resection of tumor. A variety of techniques have been brought to bear in the art with the purpose of aiding the surgeon in detecting and localizing neoplastic tissue as part of this surgical procedure. ("Neoplastic tissue", for present purposes, often is referred to as cancerous tissue, though malignant tumor and malignant tumor cells also are found in the terminology of the art. The term "neoplastic tissue" includes all of these.) A substantial amount of effort in aiding the surgeon in locating neoplastic tissue has been through the utilization of radiolabeled antibody for detection purposes. For example, one technique includes the scintillation scanning of patients injected with relatively high energy, e.g. $^{131}I$ labeled antibodies. Such photoscanning or scintillation scanning provides scintigrams difficult to interpret because of blood pool background radioactivity. Computer subtraction of radioactive blood pool agents and the use of two labeled antibodies (one specific for the tumor and one non-specific) have been attempted to enhance imaging. Nevertheless, such techniques have been found to provide little, if any, useful information to the surgeon, especially over and above CAT scans, magnetic resonance imagings, and like traditional techniques. Typically, large tumor is readily located by the surgeon by visualization at the operating theater and, in particular, through palpation, i.e. the feel of a tumor as opposed to that of normal tissue. To achieve operative success, however, it is necessary for the surgeon to somehow locate "occult" tumor, i.e. tumor which cannot be found by the conventional surgical procedure of sight and feel. Failure to locate and remove such occult tumor generally will result in the continued growth of cancer in the patient, a condition often misidentified as "recurrent" cancer. In general, conventional diagnostic techniques as, for example, use of the classic gamma camera and the like, fail to find or locate occult tumor. As tumor sites become smaller, the radionucleide concentrations at a given tumor site will tend to be lost, from an imaging standpoint, in the background where blood pool radiation necessarily is present in the patient.

U.S. Pat. No. 4,782,840 by Martin, M. D. and Thurston, Ph.D., entitled "Method for Locating, Differentiating, and Removing Neoplasms, issued Nov. 8, 1988 (the disclosure of which is expressly incorporated herein by reference) reviews such scintillation scanning technique and discloses a much improved method for locating, differentiating, and removing neoplasms. Such technique utilizes a radiolabeled antibody and a portable radiation detection probe which the surgeon may use intraoperatively in order to detect sites of radioactivity. Because of the proximity of the detection probe to the labeled antibody, the hint radiation emanating from neoplastic tissue at occult sites becomes detectable, for example, in part because of the inherent application of the approximate inverse square law of radiation propagation. The procedure is known as the Radioimmunoguided Surgery TM system (Radioimmunoguided Surgery being a trademark of Neoprobe Corporation, Columbus, Ohio) and is successful additionally because of a recognition that tumor detection should be delayed until the blood pool background of circulating radiolabeled antibody has had an opportunity to be cleared from the body. As a consequence, the photon emissions or radiation emitted by minor tumors compared to surrounding tissue becomes detectable in view of the proximity of the probe device to it. Fortuitously, the '840 patent discloses the ability of the radiolabeled antibody to remain bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand held probe positioned in close proximity with the tissue under investigation.

Somewhat recently, laparoscopic surgery has become popular as an alternative to traditional operative procedures. Particularly with the development of video-based visual systems, laparoscopic surgical techniques have been employed with more complicated gastro-intestinal procedures. Such procedures offer savings in total health care costs as a result of shorter hospital stays and a more rapid patient return to normal activity. However, these procedures require instrumentation and technique supplanting conventional three-dimensional viewing and tactile feedback to the surgeon. Improved instrumentation particularly is called for where these newer surgical techniques are applied to the detection and removal of neoplastic tissue.

While a variety of laparoscopic instruments have been developed, such equipment falls into two broad categories: those major pieces of equipment that enable the surgeon to perform laparoscopy and those instruments related to the performance of specific tasks or procedures, e.g. electrocautery and laser. Generally, visualization within peritoneal cavity requires "space" in which to shine light and maneuver. In a standard surgical approach or laparotomy this space is created by opening the abdomen and allowing room light and air into the cavity to accommodate three-dimensional viewing. In laparoscopic procedures, this is accomplished by filling the peritoneal cavity with a gas that distends the abdominal wall and provides an area for light and manipulation, a process termed "pneumoperitoneum". Carbon dioxide is the standard gas used for pneumoperitoneum. Pneumoperitoneum currently is carded out utilizing an instrument referred to as an insufflator.

Laparoscopic surgery generally features the establishment of one or more portals of entry into the abdominal cavity. Mechanisms for inserting and removing various instruments through these portals without loss of pneumoperitoneum are necessary. These ports are established by the insertion of a trochar tip through the skin of the patient in conjunction with a port defining cannula or sheath. The trocar is inserted through the lumen of the cannula as an obturator. Typically, the cannulas have a spring-loaded trumpet valve to permit the introduction of instruments into the abdomen and prevent gas from escaping. Conventionally, the size of the cannula sleeve is 1 mm larger in diameter than the corresponding instrument that will traverse it. Diameters for such instruments may reach, for example, 15 mm or larger in extent.

Employment of the laparoscopic surgical technique in conjunction with the surgical staging and resection of neoplastic tissue poses limitations heretofore not encountered by the surgeon. As noted above, when engaged in treating colon and rectal cancer, the surgeon, in addition to such aids as the radioimmunoguided systems, also relies upon sight and palpalion or feel to locate tumor. With laparoscopic surgical procedures, sight is constrained to the two dimensions available at a video screen and palpation or feel essentially is lost. In effect, the surgeon is maneuvering along or manipulating tissue through elongate instrumentation from a distance of about 18 inches away. Thus, the detection and localization of neoplastic tissue calls for laparoscopic instrumentation which effectively replaces palpalion and three-dimensional viewing. With such supporting instrumentation, the surgeon or surgical oncologist may not only seek to resect neoplastic tissue but properly stage cancer patients so that an appropriate mode of therapy can be administered. The latter staging is particularly important in view of the National Institute of Health (NIH) consensus report concerning the administration of adjuvant chemotherapy to appropriately staged patients. "NIH Consensus Conference: Adjuvant Therapy for Patients with Colon and Rectal Cancer", JAMA, 1990; 264:1444–50.

SUMMARY

The present invention is addressed to instruments for detecting and localizing sources of radiation emission and, particularly, to radiation detecting instruments employed for laparoscopic surgical procedures. Requisite response to locator retained radioactive emissions at tumor sites is achieved with the instruments, while the constraints otherwise associated with the limited size of cannula port are accommodated. Because elongated instruments usually are inserted and maneuvered generally parallel with the body plane, a more effective utilization of the radiation emission detection technique has been developed through employment of a "side looking" detector crystal mounting. With such mounting, the forward surface of the detecting crystal is oriented generally transversely to the lengthwise extent of the instrument. Thus oriented, the detector may be of rectangular configuration, having a widthwise extent limited by the correspondingly limited diameter of the instrument, but a lengthwise extent selected to provide a radiation confronting surface of sufficient area. Where cadmium telluride detectors are employed with the instrument, their noise generating microphonic attributes are controlled through an improved crystal mounting architecture.

Other objects of the invention will, in part, be obvious and will, in part, appear hereinafter.

The invention, accordingly, comprises the apparatus possessing the construction, combination of elements, and arrangement of parts which are exemplified in the following detailed disclosure.

For a fuller understanding of the nature and objects of the invention, reference should be had to the following detailed description taken in connection with the accompanying drawings.

BRIEF DESCRIPTION OF THE DRAWINGS

FIG. 1 is a perspective view of a laparoscopic instrument according to the invention;

FIG. 2 is a side view of the instrument of FIG. 1 showing components therein in phantom;

FIG. 3 is a partial sectional view of the instrument of FIG. 1;

FIG. 4 is an exploded perspective view of a crystal and associated crystal mount employed with the instrument of FIG. 1;

FIG. 5 is a sectional view taken through the plane 5—5 shown in FIG. 3;

FIG. 7 is a schematic representation of a human body showing a laparoscopic utilization of the instrument of the invention;

FIG. 8 is a schematic representation of a human body showing another utilization of the instrument of the invention;

FIG. 9 is a schematic representation of the instrument of FIG. 1 with the access tube thereof in broken fashion showing an opposite side thereof;

FIG. 13 is a partial sectional view of an instrument according to the invention which is configured for detecting beta radiation emissions; and FIG. 14 is a sectional view of the instrument of FIG. 13 taken through the plane 14—14 shown therein.

DETAILED DESCRIPTION

Figure 10:
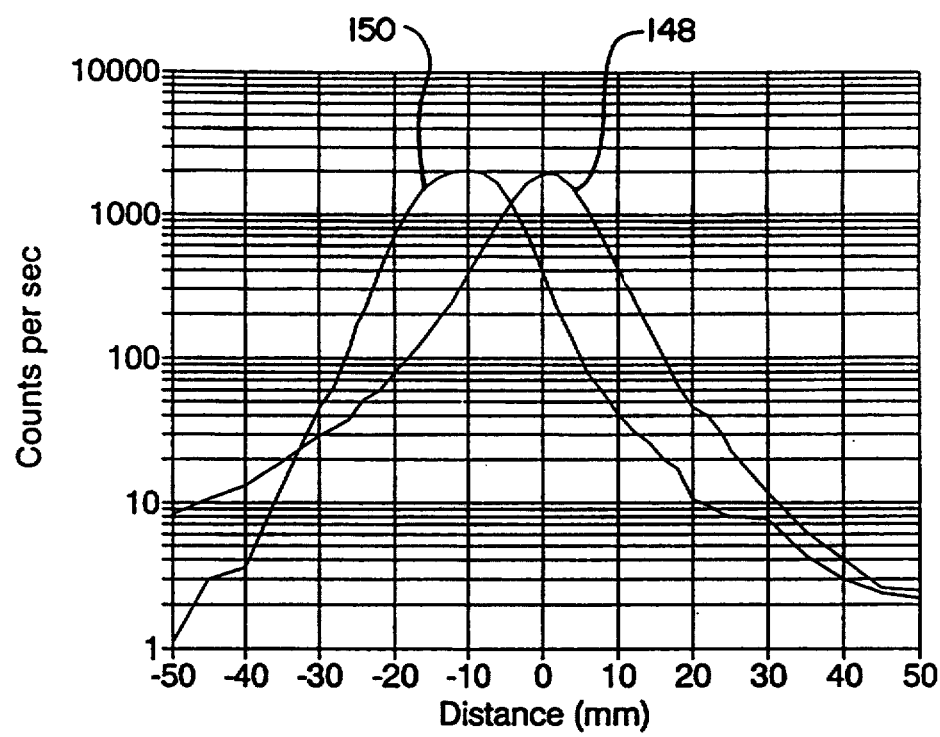
FIG. 10 is a chart showing the sensitivity of the instrument of the invention when employed for longitudinal and transverse scanning movement.

The general RIGS procedure commences with the administration to the patient of an effective amount of a radiolabelled locator which specifically binds a marker produced or associated with neoplastic tissue. A "locator" includes a substance which preferentially concentrates at tumor sites by binding with a marker (the cancer cell or product of the cancer, for example) produced by or associated with neoplastic tissue or neoplasms. Appropriate locators today primarily include antibodies (whole and monoclonal), antibody fragments, chimefie versions of whole antibodies and antibody fragments, humanized versions thereof, as well as other tumor specific carriers, i.e. locators. It should be appreciated, however, that single chain antibodies (S CAs such as disclosed in U.S. Pat. No. 4,946,778) and like substances have been developed and they primarily prove efficacious. Biochemistry and genetic engineering may yet produce substances which mimic the function of antibodies in selectively concentrating at sites of neoplastic tissue, though such substances may not be subsumed within the traditional definition of "antibody". "Locator" is a term chosen to include present day antibodies and equivalents thereof, as well as those substances yet to be determined which mimic antibodies in the method of the RIGS system.

An adaptation of radioimmunoguided surgical techniques (RIGS) to laparoscopic procedures involves a need to accommodate a variety of aspects associated with each. The hand-held radiation detecting probe employed conventionally with the RIGS system is described in U.S. Pat. No. 5,070,878 by Denen, issued Dec. 10, 1991, and assigned in common herewith. This probe utilizes a cadmium telluride crystal of adequate surface area which is mounted in a "forward looking" manner. Thus, as the probe is held by the surgeon, the window component thereof at the tip is moved transversely along tissue being evaluated. Because the RIGS surgical approach is one wherein the extent of radiation emanating from a carrier located at neoplastic tissue is quite faint, it becomes necessary that the crystal be of adequate surface area to capture sufficient radiation emissions. Of similar importance, because of the rapid fall-off of radiation as the crystal surface is moved away from that tissue region in consequence of the inverse square law of radiation propagation, it is essential that the surgeon maintain a close proximity between the crystal surface behind the probe window and the radioactive tissue. In effect, this application of the inverse square law of radiation propagation aids in sharply delineating the extent or boundaries of neoplastic tissue. Collimators obviously are not employed with such a system where low energy radiation is involved inasmuch as they would not sharpen the location of radiation but would lessen the number of received emissions from the faint radiation source at the tumor site. From the laparoscopic surgical standpoint, it is necessary that the laparoscopic instrument be maneuverable, having an access tube or the like of diameter limited by the port of a cannula, for example, less than 12 mm. In the development of the instant invention, it was determined that the latter diametric constraint imposed unwanted limitations on the available surface area of a radiation detecting crystal such as cadmium telluride. As a forward looking laparoscopic adaptation of the radiation detecting probe was employed, in addition to the low count rates available with smaller diameter crystals, as the source of radiation was approached, usually in a longitudinal direction along the body cavity, instrument response diminishes as the crystal moves across the radiation source because of the shielding positioned about the crystal itself. Transverse movement of the instrument within the body cavity, for example, from a vertical orientation, represents a procedure with serious limitations to the extent it is not desirable. Thus, the laparoscopic instrument is required to be configured within the diametric constraints associated with its insertion through a cannula and its somewhat horizontal maneuvering within the body cavity. Next, the device must be capable of retaining a crystal such as cadmium-zinc-telluride for detection which has adequate surface area to achieve operationally effective radiation detecting sensitivity. This instrument then is called upon to locate neoplastic tissue through faint radiation emissions while being observed two-dimensionally with a television camera which also is inserted through a cannula into that same body cavity. In effect, the instrument is called upon to replace the surgeon's sense of touch and to support the surgeon's vision which now is restricted to two dimensions.

Referring to FIG. 1, a laparoscopic instrument incorporating the features of the invention is revealed in general at 10. Instrument 10 includes a hand-grippable cylindrical base portion 12 to which an elongate accessing tube 14 is fixed. Accessing tube 14 is of a length convenient to the surgeon for accessing those regions of the abdominal cavity intended for neoplastic tissue detection and localization. This length may, for example, be about 14 inches (36 cm) and extends to a tip 16.

Inwardly from this tip 16 there is a detector support portion represented generally at 18 which extends to a union or joint represented at line 20. Tube 14 is cylindrical, having an outer diameter, for example, of 11 mm such that it is suitable for insertion through a conventional 12 mm diameter cannula port. This cylindrical configuration extends through to the tip 16, however, the detector crystal mounted within the instrument 10 provides for "side looking" evaluation of impinging radiation. This is through a planar or flat window 22 located at the detector support portion 18 and which is seen to have a somewhat elongate rectangular peripheral shape. The crystal detector which will be seen to be spaced but closely proximate the window 22 is operated in conjunction with signal treatment and control circuitry which ultimately is coupled through a console mounted connector (not shown) to the instrument 10 via a shielded flexible cable 24 extending from the hand-grippable base 12. In general, the control and signal treatment components are contained within a console to which the cable 24 leads and which is located out of the sterile surgical field. However, some signal treatment components are necessitated at the instrument 10 itself. Looking additionally to FIG. 2, a crystal mount arrangement is shown in general in phantom at 26 located within the accessing tube 14 at the detector support portion 18. Located in adjacency with the crystal mount 26 is a preamplification stage represented generally at 28. Depending upon the constraints of the size of the passageway within tube 14, it may be found appropriate to split the preamplification function of the instrument 10 into two components. Accordingly, a forward stage 28 is positioned in proximity to crystal mount 26 and stage 28 then communicates, for example, with shielded cable as represented by dashed line 30 with a second or final preamplification stage shown in phantom at 32 which is mounted within the hand-grippable base 12. Cable 24 is electrically connected with this last amplification stage represented at 32.

Looking to FIGS. 3 and 4, the structuring of the crystal mounting arrangement 26 is revealed at an enhanced level of detail. In the figure, a crystal mount 34 which is formed of a material selected to attenuate gamma radiation such as lead is provided which is inserted within the passageway of rod 14 at the detector support portion 18. This mount 34 is seen to be generally cylindrical in shape with a flattened or truncated upwardly disposed surface 36 and a stepped down surface portion 38. Formed inwardly from the flat surface 36 is a rectangular crystal receiving and supporting cavity 40. The mount 34 is seen to be positioned within a separate or discrete cylindrical tip component 42 of the tube 14. In this regard, the component 42 is seen to be flattened to define the window surface 22 and is slidably mounted over a stepped down surface 44 (FIG. 3) turned within tube 14. Retention of this tip component 42 upon the stepped down surface 44, for example, is provided using an electrically conductive epoxy cement. In this regard, the connection must be such as to assure no leakage of body fluids within the passageway 46 formed within tube 14. Note that the upwardly disposed flat surface 36 of the mount 34 is spaced in close adjacency with the underside of the window component 22 of tip component 42. This permits the positioning of a radiation responsive crystal as close as possible to that surface window 22. FIG. 3 shows an opening or conduit 48 formed within the mount 34 which extends from an opening 50 within the rearward surface of mount 34 to a corresponding opening 54 at the bottom surface of cavity 40.

The configuration thus depicted in connection with FIGS. 3–5 is one intended for use in detecting locators labeled with gamma emitting radiation, and, particularly, emitted from $^{125}I$ which, for the surgical performance contemplated will be of very low energy level. Cadmium-zinc-telluride detecting crystals are employed for this purpose. Such crystals are marketed by Aurora Technologies, Inc., San Diego, Calif. For the present laparoscopic instrument, it is desirable that the crystal used for detection have as large a surface area as is practical to improve counting efficiency. Preferably, that active surface area will be equivalent to the surface area of forward looking crystal mounts as are used in conventional RIGS surgery. To achieve this requisite active surface area while maintaining necessarily restricted instrument diameters, a rectangular cadmium-zinc-telluride crystal 60 is employed having a principal lengthwise dimension in parallel with the central axis 62 of the tube 14. Because cadmium telluride crystals exhibit microphonic (piezoelectric) effects, their mounting for the instant use requires a rigid avoidance of noise generated by rubbing or by the transmission of acoustical noise or the like into the crystal 60 from its mounting environment. To achieve this requisite mounting with an avoidance of microphonic induced noise, the cavity 40 is initially covered with an electrically insulative polymeric layer 64. Preferably, the layer 64 is formed of silicone, generally referred to as silicone rubber which is an elastomer in which the C linkages of a polymerized hydrocarbon are replaced by Si—O linkages. It is sold, for example, under the trademark "SILASTIC". In this regard, the layer 64 can be developed as a rectangular receptacle with a rectangular mold carrying a conventional mold release. A necessary electrical bias, for example at 60 v, is asserted at the rearward surface 66 of the crystal 60 by an electrical contact arrangement including multi-strand wire 68 seen extending from connection with a circuit board 70 in FIG. 3 and through the opening 50 of passageway 48 to opening 54 within the cavity 40. From this opening 54, the plurality of strands of this wire are "spread out" over the polymeric layer 64 as seen in general at 72 in FIG. 4. Additionally, positioned over the electrically insulative polymeric layer 64 at the bottom of the cavity 40 is an electrically conductive cushion layer 74 having a lower disposed surface 76 positioned over the strands 72 and upon the forwardly facing surface of layer 64. To avoid microphonically induced noise, this lower disposed surface 76 of the cushion layer 74 is adhered to the upper surface of the heat-stable silicone rubber. Additional amounts of the "SILASTIC" material may be used for this purpose. Advantageously, the electrically insulative elastomeric adhesive retains its elastic properties over time and high temperature conditions. With the arrangement thus shown, electrical bias, as well as electrical communication with respect to charge transfer is asserted from the contact strands 72 into this electrically conductive cushion layer to its upwardly disposed surface 78. Preferably, the electrically conductive cushion layer 74 is provided as a non-woven TEFLON cloth which is carbon filled to the extent rendering it an effective conductor of electricity. In general, the material is a carbon containing stretched, highly crystalline, unsintered polytetrafluoroethylene marketed under the trademark "Gore-Tex".

The lower or rearward surface 82 of the cadmium-zinc-telluride crystal 60 is freely abuttably positioned over the upwardly disposed surface 78 of electrically conductive cushion layer 74. No adhesive is employed in this union other than some of the silicone adhesive may migrate about the edge of the crystal 60 with beneficial effect. This positions the upwardly disposed surface of crystal 60 as at 84 in close adjacency with the underside of the window 22. To retain the assemblage of crystal 60 and associated mount in position, a thin elastomerically deformable sheet 86 is stretched over the assembly including the upwardly disposed surface 84 of crystal 60. This compressibly urges the crystal 84 downwardly to improve device performance. The thin sheet 86 may be provided as a carbon-filled rubber and thus serves the second purpose of asserting necessary ground at the surface 84 of crystal 60. Note in this regard, that in stretching the sheet 86 over the crystal 60, it is fastened by machine screw and washer combination 88 at the forward or tip portion 90 of mount 34 seen in FIG. 3. The opposite end of the sheet 86 is similarly fastened to surface 38 of mount 34 by a machine screw and washer arrangement shown at 92 in FIGS. 3 and 4. Ground is conveyed to the sheet 86 from the lead mount 34 which, in turn, is coupled to ground through the forward stage 28 of the preamplifier function. Note that the circuit board 70 is seen attached to surface 38 of mount 34 with a screw 94.

Figure 6:
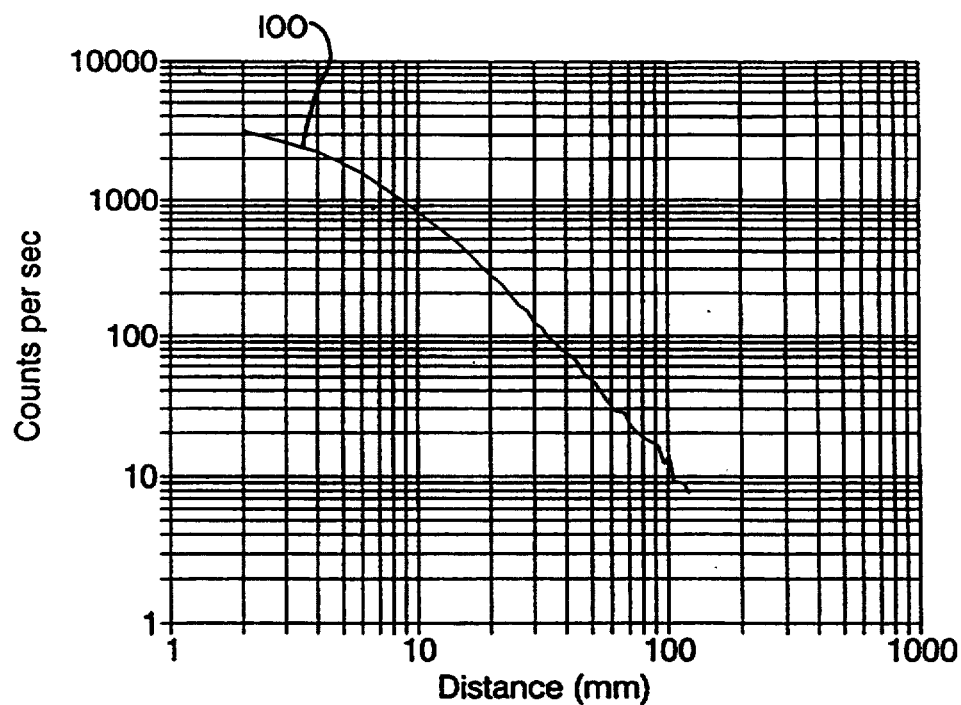
FIG. 6 is a graph showing the sensitivity of the instrument of FIG. 1 in counts per second with a distance of its detector component from a source of radiation.

Thus mounted within the detector support region 18 of instrument 10, the upwardly disposed surface 84 of crystal 60 is spaced from the underside of window 22 by a very small gap 96 to avoid acoustic or vibrationally induced noise. However, the distance from the outwardly disposed surface of window 22 to that upwardly disposed surface of crystal 60 is quite small, being, for example, less than 2 mm. This permits the upwardly disposed surface 84 of crystal 60 to be positioned in very close proximity to the tissue under investigation. It is the flatness of the window 22 within the generally cylindrical instrument 10 which additionally permits this close positioning of the crystal to the tissue under investigation. Such distancing for the purpose of the operation of instrument 10 is quite important in view of the low level of radiation involved and the noted approximate inverse square relationship of radiation propagation. Looking momentarily to FIG. 6, the sensitivity of instrument 10 with respect to distance from a radiation source as may be encountered is revealed. The figure shows a curve 100 generated employing a 1 microcurie source ($^{129}I$). That source gradually is positioned further and further away from the upward surface 84 of crystal 60. Note that at a 2 mm distance, representing the equivalent of positioning the source right at the top surface of window 22, a count of about 3,000 counts per second is recognized. However, that initial count at the closest proximity to window 22 is seen by curve 100 to drop to 2,000 counts per second at the close distance of about 4 mm from the source. This rapid fall-off demonstrates the importance of the flatness of window 22 and its close positioning in adjacency with the top surface 84 of crystal 60.

The effectiveness of the "side-looking" orientation of the crystal 60, i.e. generally in parallel with axis 62 of instrument 10 may be recognized in connection with conventional laparoscopic procedures. Looking to FIG. 7, a schematic representation of the human anatomy is provided.

In FIG. 7, the horizontal body 110 is depicted having a liver region 112 in the vicinity of the rib cage. In this region is the gastrohepatic ligament with associated lymph nodes about the portal region of liver 112. These nodes are currently the subject of substantial interest on the part of those employing the RIGS system. Below the liver region 112 is the colon. The colon is 120–200 cm long. The ascending colon is shown at 114 extending from the iliac fossa to the inferior surface of the liver 112. Then, the transverse colon 116 extends to the descending colon 118 thence to the sigmoid colon 120, the latter being suspended by its mesentery. In the figure, the instrument 10 is reproduced having been inserted through a cannula 122 located below the umbilicus. The detector support portion 18 of instrument 10 is seen scanning somewhat horizontally both transversely and longitudinally a tumor region 124 while being observed by a laparoscope or video camera 126 which has been inserted through cannula 128 above the umbulicus. Other ports typically will be opened within the body 110 following pneumoperitoneum. Thus, as the surgeon grasps the instrument 10 at its base 12, it is maneuvered about the region of interest while being observed in two-dimensional color television at a video monitor positioned adjacent the surgical theater.

FIG. 8 shows a similar procedure in conjunction with a body representation utilizing the same numeration for identification as shown in FIG. 7. For this procedure, the instrument 10 has been inserted through a cannula 140 below the umbilicus but positioned so as to permit scanning of the descending colon 118, particularly with respect to a tumor region represented at 142. To observe this scanning operation through a television monitor, the laparoscopic camera 126 is inserted through a cannula 144 such that it may be positioned to observe the detector support portion 18 of instrument 10 as it scans about the region of interest 142. It has been found desirable to provide a visual televised readout of the rotational orientation of the instrument 10 during such procedures. Looking momentarily to FIG. 9, a thin line 146 may be seen to be engraved along the back surface of the accessing tube 14 including its detector support portion 18. This line may be observed by the video camera 126 and is seen to extend to the base portion 12 such that it may be observed also by the surgeon outside of the body cavity. The line 146 is positioned along the instrument opposite the center of planar window 22.

Referring to FIG. 10, the output of the instrument 10 with respect to the noted transverse scanning and longitudinal scanning is revealed at respective curves 148 and 150. The same source and general set-up as described in connection with FIG. 6 was used in a laboratory setting. The cadmium telluride crystal 60 employed with the instrument 10 had dimensions of 7 mm × 14 mm. To derive the curve 148 for a transverse scan, the source was moved from the center position of the window 22 and outwardly therefrom. This center position, located at distance "0" shows a somewhat sharp peak in the resultant output in counts per second which may be expected from the shorter widthwise dimension of the crystal. To derive curve 150, the outer tip 16 of the probe was established as a 0 position, thus the curve 150 is shifted with respect to curve 148 and exhibits a wider peak response which is in keeping with the greater principal longitudinal dimension of the cadmium telluride crystal 60.

Figure 11A:
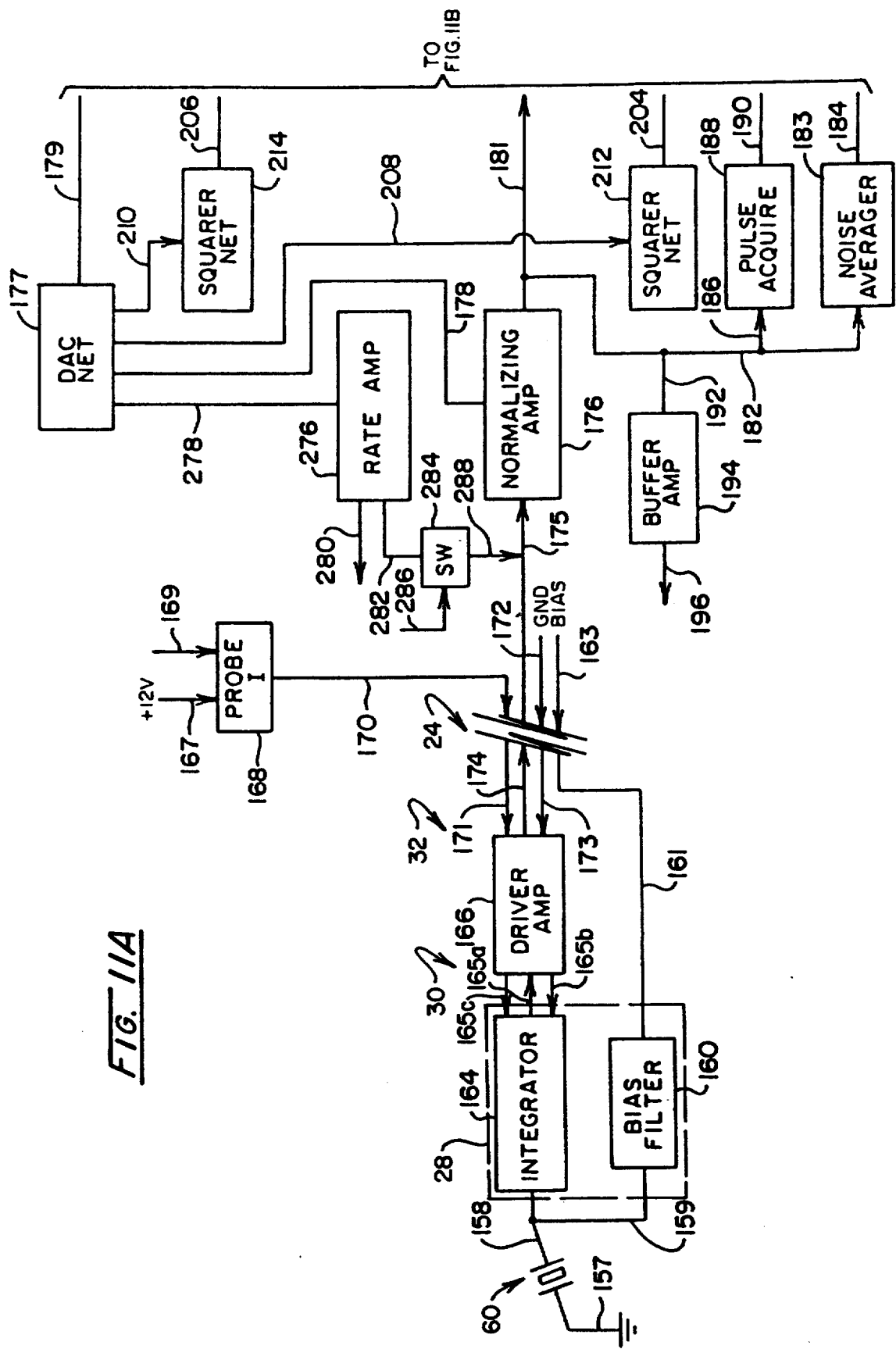
FIGS. 11A and 11B combine as labeled to form a block diagram of the functional components of a signal treatment and control system associated with the instrument of the invention.
Figure 11B:
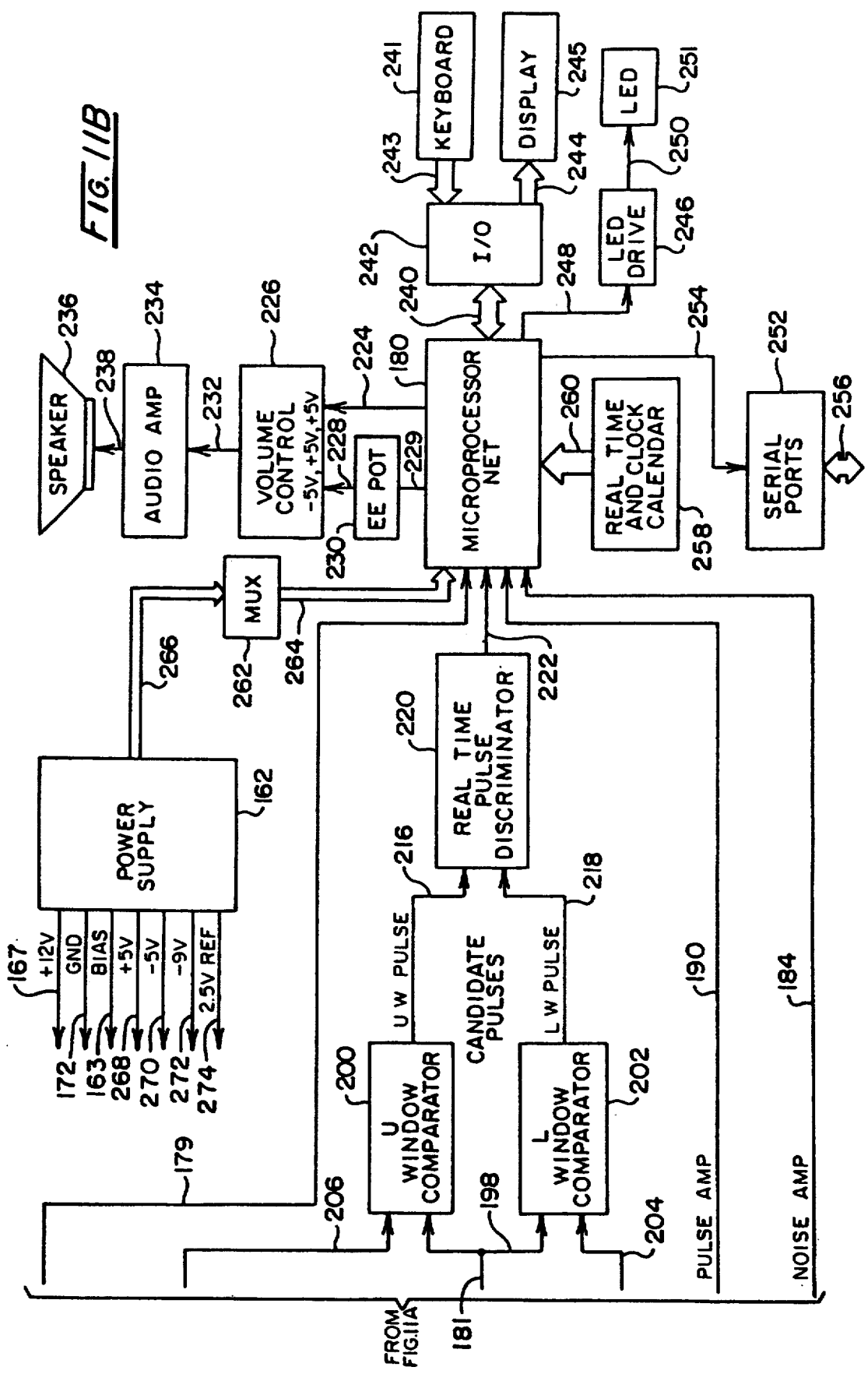

Referring to FIG. 11A and 11B, a block diagrammatic representation of the signal treatment and control circuitry employed with instrument 10 is revealed. In FIG. 11A, that crystal which is being employed, for example crystal 60 as labelled, is shown having one face coupled to ground through line 157, while the opposite, biased face thereof is coupled via lines 158 and 159 to a bias filter represented at block 160. Bias filter 160 is part of the earlier-described forward preamplification stage 28 herein identified in FIG. 11A by a dashed boundary with the same numeration. The input to the filter 160 is derived ultimately from cable 24 (FIG. 1) and is represented in FIG. 11A at line 161 as being applied through that cable again represented by numeral 24. Line 158 corresponds with line 68 earlier described in connection with FIG. 3 and supplies an appropriate bias, for example, 60 v to the rearward surface of crystal 60. This bias emanates from a power supply shown at block 162 in FIG. 11B and represented at line 163.

Line 158 from crystal 60 is shown extending to an integrator stage 164 of the first preamplifier stage 28. The integrated valuation of a detected radiation disturbance or charge categorized signal then is shown directed as represented by line 165a to a driver-amplification network shown at block 166. Line 165a additionally is a part of the shielded cable 30 extending through the passageway 46 of access tube 14 to the second preamplification stage 32 within base 12 as described in connection with FIG. 2. Cable 30 also may carry ground and +12 v supply as shown, respectively, at lines 165b and 165c. The noted 12 v power supply as represented at line 165c is derived for the driver amplifier stage 166 from the power supply 162 (FIG. 11B) as represented at line 167 which, as shown in FIG. 11A, is directed to a probe current network represented by block 168. Under microcomputer control as represented by line 169, the network 168 develops signals, for example, determining whether the probe instrument 10 has been properly connected to a console based control system described in detail in U.S. Pat. No. 4,801,803 (not shown). Delivery of the 12 v power supply for the preamplifier stage 32 is represented at line 170 as extending to the driver-amplifier 166 via cable 24 and line 171.

Ground to the instrument 10 also is developed from the power supply block 162 as represented at line 172 shown in FIG. 11A as extending to cable 24 and via line 173 to the driver-amplification stage 166.

The output of the driver-amplification stage 166 is represented at line 174 extending through the cable 24 and then being represented as line 175 to the input of a normalizing amplifier represented at block 176. The network represented by block 176 functions to amplify or attenuate, i.e. scale the noise characteristic of any given instrument 10 and normalize the value thereof or render it consistent for later comparison stages. Generally, for example, the 27 key energy level gamma ray generated pulses in a system employing $^{125}I$ will be about five times higher than noise levels. Normalizing amplifier network 176 will establish those noise levels at some predetermined level, for example, 200 millivolts, and the resultant proportional valid gamma related pulses will become about 1 v high for purposes of ensuring comparison functions. It may be observed that the amplifier network at block 176 is controlled from a digital-to-analog converter network represented at block 177 via line 178. Network 177, in turn, is controlled from line 179 extending, as shown in FIG. 11B, to block 180 representing a microcomputer network. The normalized output developed from network 176 is presented along lines 181 and 182 to a noise averager circuit as represented at block 183. This network 183 determines an average amplitude value for the noise of a given system with a given instrument 10 and provides a corresponding signal as represented at line 184 (noise amp) which is employed as above described as information used by the microcomputer 180. This information, in addition to being employed with the normalizing amplifier network represented at block 176, may be used to develop a low window valuation for the comparison function.

Line 182 also extends via line 186 to a pulse acquire network represented at block 188. This network functions, when activated, by the microcomputer represented at block 180, to acquire the value of the highest pulse amplitude witnessed at line 186. Periodically, this information then is transmitted to the microcomputer at block 180 as represented by line 190. Representing a form of peak detector, the network is sometimes referred to as a "snapshot circuit". Also produced from line 182, as at line 192 and block 194, is a buffer amplifier which will provide at line 1.96 an output representing received pulses which may be made available to the system, for example, at a console (not shown).

Line 181 extends, as shown at FIG. 11B, at line 198, to one input of an upper window comparator represented at block 200 and a lower window comparator illustrated at block 202. The threshold level for comparative purposes employed by the network at block 202 is shown asserted from line 204 and, preferably, is developed by the logic of microcomputer network 180 at a level just above the noise amplitude signals generated from line 184. Of course, manual setting of such windows can be carried out. In similar fashion, the upper window of acceptance for valid radiation interaction is established from a corresponding line 206. This threshold setting may be made from the information taken from pulse acquire network 188.

Returning to FIG. 11A, the upper window and lower window threshold selections are made under the control of the microcomputer network at block 180 which controls the digital-to-analog network shown at block 177. It is the characteristic of such networks as at block 177 to provide an output which is comprised, for example, of 256 steps of varying amplitude. The percentage of incrementation from step to step will vary somewhat over a range of voltage values provided. Accordingly, the outputs from this conversion network at block 177, as shown at lines 208 and 210 are directed to squarer networks shown, respectively, at blocks 212 and 214. These networks function to square the current outputs at lines 208 and 210 and thus achieve a uniform percentage incrementation of the threshold defining outputs at lines 204 and 206.

Returning to FIG. 11B, the outputs of the comparator networks shown at blocks 200 and 202 represent candidate pulses which may be above or below the given thresholds and are identified as being presented as "UW pulse" and "LW pulse" along respective lines 216 and 218. These lines are shown directed to a real time pulse discriminator network represented at block 220 which carries out Boolean logic to determine the presence or absence of valid pulses. Valid pulses are introduced to the microcomputer network 180 as represented by line 222.

The microcomputer network represented at block 180 performs under a number of operational modes to provide both audio and visual outputs to aid the surgeon in locating and differentiating tumorous tissue. In the former regard, as represented at line 224 and block 226, a volume control function may be asserted with amplitude variations controlled from a solid-state form of potentiometer represented at line 228 and block 230. Control to potentiometer 230 is represented at line 229. Further, a "siren" type of frequency variation may be asserted as represented at line 232 to an audio amplification circuit represented at block 234 for driving a speaker as represented at 236 and line 238. With the noted siren arrangement, the frequency output from speaker 236 increases as the instrument 10 is moved closer to the situs of concentrated radiation. Of course, conventional clicks and beeps can be provided at the option of the operator.

The microcomputer network 180, as represented by bus defining arrow 240 and block 242 also addresses an input-output network which, as represented at bus arrow 244, functions to provide a pulse count output of varying types as well as outputs representing volume levels, pulse height, noise levels, and battery status. These outputs are provided in visual format at a visual display represented at block 245. Similarly, the input-output function represented at block 242 provides appropriate scanning of switches or the like may be employed with the control system and are represented by block 241 and bus input arrow 243. During a given counting operation, the microcomputer network at block 180 functions to control a light emitting diode drive network represented by block 246 from line 248. The drive network represented at block 246 is shown providing an input, as represented by line 250, to a light emitting diode (LED) display as represented by block 251. A serial output port of conventional variety also may be provided with the system, such ports being represented at block 252 being addressed from the microcomputer represented at block 180 from line 254 and having output and input components represented by arrow 256. A real time clock-calendar having a non-volatile memory also may be provided in conjunction with the functions of the microcomputer network 180 as represented by block 258 and bus-arrow 260. Further, the microcomputer may be employed to monitor the performance of the power supply represented at block 162. This is shown being carded out by the interaction of the microcomputer network with a multiplexer represented at block 262 and having an association represented by arrows 264 and 266. It may be observed that the power supply also provides a +5 source for the logic level components of the circuit as represented by line 268; a −5 source at line 270, as well as a −9 v source at line 272 for purposes of display drive, and finally, a 2.5 v reference as represented at line 274 to provide reference input for the preamplification analog circuitry.

Returning to FIG. 11A, the microcomputer network as represented at block 180 also provides an input to the digital-to-analog conversion network represented at block 177 which corresponds with the instantaneous pulse rate and this information is conveyed to a pulse rate and this information is conveyed to a pulse rate amplifier network represented at block 276 via line 278. The resultant output, as represented at line 280, may be provided, for example, at a convenient location upon a console. This circuit represented at block 276 also may be employed to generate a calibrating pulse for testing the downstream components of the system. Thus, the microcomputer represented at block 180 applies a predetermined pulse level through the digital-to-analog conversion network at block 177 for presentation to the amplifier network represented at block 276. The resultant output at line 282 is selectively switched, as represented by block 284, to define pulse width from the microcomputer input at line 286 to the calibrating pulse at line 288.

Figure 12:
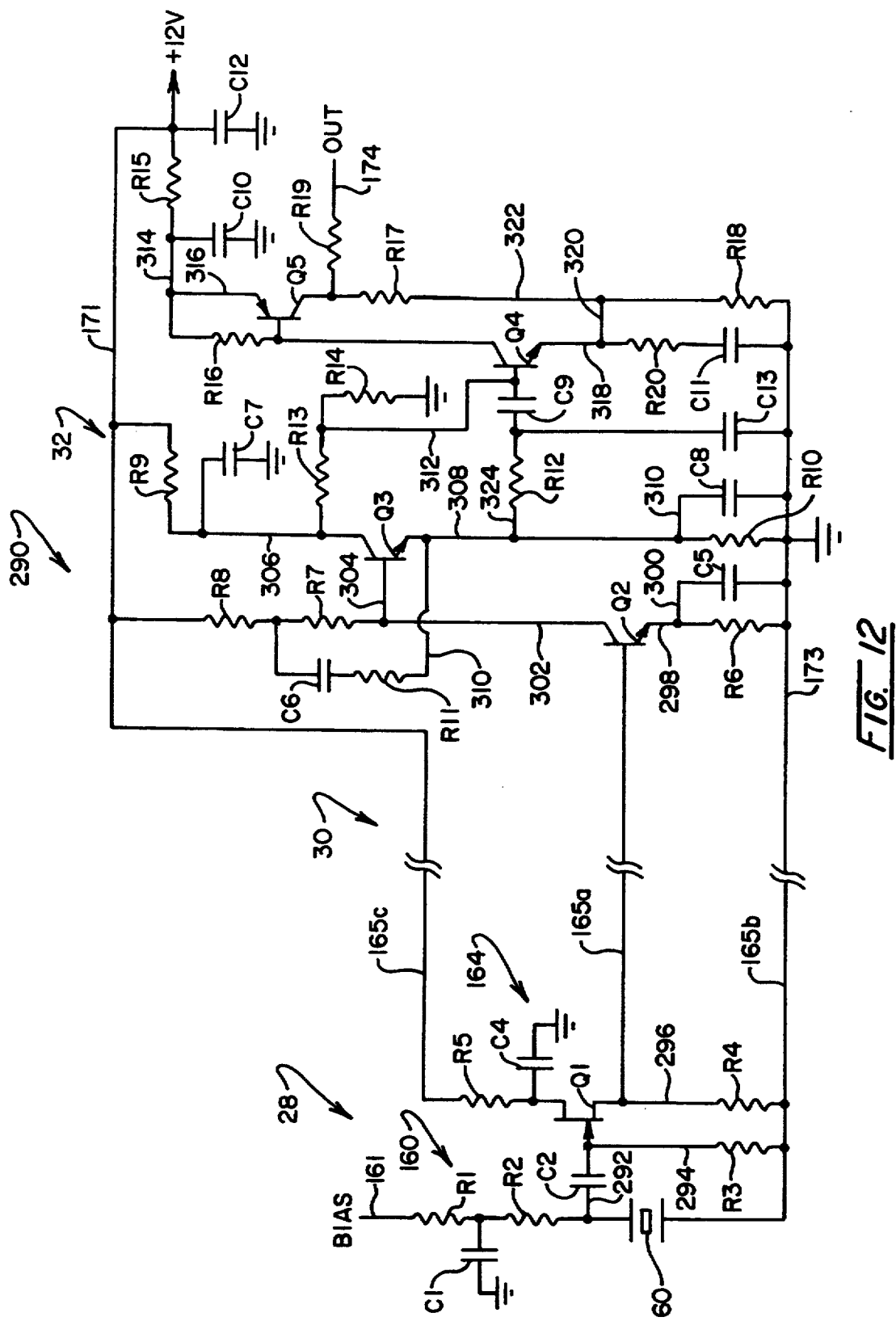
FIG. 12 is an electrical schematic diagram of a preamplification function employed with the instrument of the invention.

Referring to FIG. 12, the dual stage preamplification function employed with the instrument 10 is represented generally at 290. The preamplification function 290 includes the earlier-described forward stage 28 which is coupled by a shielded connector 30 to a second stage again represented in general at 32. The circuit 290 is seen performing in conjunction with a radiation detecting crystal herein again represented at 60 and is seen to include a bias filtering component as earlier described and again represented in general at 160 as well as an integrator component 164 again represented by that numeration. The components of the cable 30 are represented as described in conjunction with FIG. 11A at lines 165a–165c. Bias, as before, is shown being provided from line 161. This bias is seen to be asserted through one side of crystal 30 through the bias filter 160 comprised of resistors R1, R2, and a capacitor C1. Capacitor C1 provides a local filter to remove any spurious noise which may be engendered in the line transmitting bias. The opposite face of crystal 60 is coupled to ground as represented by earlier-described line 165b. Crystal bias resistor R2 is provided having a large resistance value, for example, about 50 megohms, a level selected to avoid absorbing current disturbances from the crystal. The input signal to the integration stage 164 is asserted through coupling capacitor C2 and line 292 to the gate input terminal of a N-channel junction field effect transistor (JFET) Q1. Line 292 also is coupled via line 294 and bias resistor R3 to ground at line 165b. The resistance value at resistor R3 is selected commensurately with the selection of resistance for resistor R2, preferably about 200 megaohms to avoid signal absorption. Generally, the resistance for this component will be selected between about 10 to 10,000 megaohms. As an integrator component, the transistor Q1 performs with stray capacitance and, additionally, in effect, operates as a source follower charge amplifier, its purpose being to achieve an impedance transformation from a very high impedance gate suited to low current and low noise. In general, the JFET structure exhibits lowest current noise at the room temperature operating conditions contemplated for the present instrument. Further, these exhibit high frequency response (wide band width) as well as a high amplification factor or high transconductance. In view of the latter aspect, the device tends to create a large current disturbance at its source terminal at line 296. Line 296 extends through a source load resistor R4 to ground line 165b. The resistor R4 functions as a d.c. current return device. The drain terminal of transistor Q1 is coupled to +12 supply at line 165c while the same terminal is decoupled or isolated by a filter comprised of capacitor C4 and resistor R5.

The charge categorized output of stage 28 at line 165a is transmitted along the cable 30 and line 165a to the base of NPN, bipolar transistor Q2. Transistor Q2 performs a voltage amplification and a singular bipolar component is elected for this function inasmuch as such devices exhibit low voltage noise characteristics at room temperature. Additionally, the devices have a higher amplification factor availability than corresponding field effect transistors.

The degree of amplification achievable with stage Q2 is related to the impedance exhibited with respect to its emitter and collector, i.e. the value of the collector load impedance divided by the emitter impedance. In the arrangement shown, the emitter of transistor Q2 is coupled via line 298 to ground through resistor R6 and is by-passed to ground via lines 298 and 300 through capacitor C5. The latter component exhibits relatively low impedance on the order of 25 ohms at the frequencies of interest. The collector of transistor Q2 is coupled with +12 supply via line 302. Line 302, in turn, is associated with a relatively high resistance value resistor R7 which is in series with a resistor R8. To enhance gain, an NPN transistor Q3 is coupled in a "bootstrap" circuit arrangement to raise its effective collector impedance to transistor Q2. In this regard, the base of transistor Q3 is coupled via line 304 to line 302, while the collector thereof at line 306 is coupled to supply line 171 in conjunction with a decoupling filter comprised of resistor R9 and capacitor C7. The emitter of transistor Q3 is coupled to line 308 to ground through resistor R10 as well as via line 310 incorporating resistor R11 and capacitor C6. This line 310 extends to a position intermediate resistors R7 and R8. Transistor Q3 functions as an emitter follower, feeding the noted junction between resistors R7 and R8 through resistor R11 and capacitor C6 in bootstrapping fashion. Resistor R11 is incorporated in the circuit to damp the positive feedback and lower gain otherwise elevated due to the stage separation of the preamplification function 290. Transistors Q2 and Q3 may be considered to participate in the integration function 164, however, for the instant description, they are incorporated within what has been referred to as a driver amplifier function 166. The signal at line 308 is applied through resistor R12 and capacitor C9 to the base of an NPN transistor Q4 which forms one component of an amplification stage in conjunction with PNP transistor Q5. This A.C. voltage amplifier comprises few components and exhibits high gain and broad bandwidth characteristics. Because the gamma ray interaction at crystal 60 will exhibit a frequency disturbance spectrum ranging from about 50 KHz to 200 KHz, the frequency response of this amplification component is tailored accordingly. For example, the high end roll-off of the response is established by resistor R10 within line 308 and capacitor C8 within line 310.

A voltage bias to the base of transistor Q4 is provided via line 312 from supply following its division by divider resistors R13 and R14. This bias input, amounting to about $\frac{1}{4}$ of the supply voltage is treated by the filter combination of resistor R9 and capacitor C7.

The 12 power supply additionally is filtered by a pi filter comprised of capacitors C10 and C12 along with resistor R15 as coupled within line 314. Line 314, in turn, is seen to extend via line 316 to the emitter of transistor Q5 and through resistor R16 to the base thereof as well as to the collector of transistor Q4. Correspondingly, the emitter of transistor Q4 extends via lines 318, 320, and 322 to resistor R17 and the collector of transistor Q5 as well as to resistor R18. The output of the preamplifier function 290 is provided at earlier-described line 174 incorporating resistor R19. The gain of this output stage is set by resistor R20 in conjunction with resistor R17, while capacitor C11 aids in the setting of low frequency roll-off for the amplifier component. The high frequency roll-off characteristic is further aided by the combination of resistor R12 and capacitor C13, the latter component being coupled between line 324 and ground via line 326. Low end roll-off characteristics for the amplification stage further are aided by the combination of capacitor C5 and resistor R6.

For the RIGS surgical procedure, in addition to the utilization of radioisotope tags emitting gamma radiation, radioisotopes emitting beta radiation additionally can be used in conjunction with the laparoscopic instrument of the invention. However, the instrument will employ a crystal semi-conductor responsive to beta radiation emissions or positrons. Beta radiation responsive devices intended for interoperative use are disclosed, for example, in U.S. Pat. No. 5,008,546.

In the discourse to follow, instrument components common to FIGS. 1–5 are identified with the same numeralion in FIGS. 13 and 14. While the surgical technique utilizing a laparoscopic probe instrument remains the same, the beta responsive device will be altered; however, it will be able to perform with the same supporting circuitry.

Referring to FIG. 13 and 14, the instrument 10 is revealed having an access tube 14 as before incorporating a passageway 46 and at least one initial stage of a pre-amplification function as represented at 28 in conjunction with a thin elongate circuit board 340. The detector support portion 18 of the instrument 10 now is configured somewhat differently, having an outer cylindrical support housing 342 which may be formed of aluminum or plastic and which is attached to a surface 344 of reduced diameter at the end of tube 14. In general, the housing 342 is attached by an epoxy adhesive which, for the present embodiment, should be electrically conductive. Housing 342 forms a tip 346 and extending inwardly from that tip in generally parallel relationship with the central axis 348 of the instrument is a rectangular opening 350 defined by the peripheral edges as at 352. Over this opening 350 there is positioned a thin polymeric cover 354 having a thickness, for example, of 4 mils and being vapor coated with aluminum to provide opacity within the interior of the housing 342 while remaining substantially transmissive to beta radiation to define a window at opening 350. The cover 354 may be provided as a thin polyester, for example, such as that sold under the trademark "Mylar". Preferably, a detector or crystal component is selected which is responsive to beta or positron emissions while remaining non-responsive to gamma radiation. Such a component may be provided as a silicon crystal configured with a PN junction, the latter being reverse biased to evoke a depletion layer. Such a crystal is represented in the figure at 356 positioned within a rectangular cavity 358 formed within a crystal mount 360. Mount 360 is fashioned of a material which attenuates beta radiation without the generation of secondary X-rays. Accordingly, the device is made of a plastic or the like and specifically not a heavy metal such as lead. A polycarbonate may be used for the purpose of device 360. Mount 360 appears quite similar to that described at 34 having a flat upper surface 362 which is again stepped down at 364 for the purpose of supporting elongate circuit board 340 through a screw connection 366. As before, a conduit 368 extends through mount 360 from an opening 370 within the passageway 46 to an opening 372 at the bottom center of cavity 358. Silicon device 356 will not exhibit the microphonic noise effects of a cadmium telluride device, consequently, its mounting is somewhat simplified. In this regard, a silicone or silicone rubber layer 374 is formed along the walls of cavity 358, for example, as before, utilizing a mold and mold release. Connection of the lower crystal surface 380 of silicon crystal 356 with a biasing lead as at 376 may be provided through an electrically conductive adhesive or by thermal compressive bonding. In similar fashion, the ground connection to the upper surface 382 of crystal 356 may be provided by an aluminum wire as at 378. Aluminum is used for this purpose to avoid X-ray generation and may be coupled into surface 382 by thermal compression bonding.

Since certain changes may be made in the above-described apparatus without departing from the scope of the invention herein involved, it is intended that all matter contained in the description thereof or shown in the accompanying drawings shall be interpreted as illustrative and not in a limiting sense.

We claim:

1. An instrument for detecting and locating a source of radiation emission, comprising:

an elongate housing extending along a centrally disposed longitudinal axis to a tip, having a side looking window region extending rearwardly from said tip with a flat, window arranged substantially parallel to said axis through which said radiation emission is transmissible;

a radiation responsive crystal having a generally rectangularly shaped periphery with a longitudinal dimension along said axis and a widthwise extent less than said longitudinal dimension having a rearward surface and an oppositely disposed forward surface facing outwardly from and substantially parallel with said axis in side looking fashion, said longitudinal dimension and said widthwise extent providing an area of said forward surface effective to respond to radiation transmitted through said window to derive charge outputs having peak levels when said crystal is substantially centered with respect to said source of radiation emission;

a crystal mount supported by said housing in adjacency with said window formed of material attenuating radiation, having a cavity for receiving said crystal and locating said forward surface in closely spaced substantially parallel adjacency with said window, said cavity having an interior surface with a periphery corresponding with said crystal periphery to provide for response only to radiation transmitted through said window;

an electrically insulative elastomeric polymeric layer positioned over said receiving cavity interior surface;

an electrically conductive deformable cushion layer with an upwardly disposed surface, said layer having a lower disposed surface which is located in abutment with said electrically insulative layer and adhered thereto with an elastomeric adhesive;

an electrically conductive contact assembly having a forward portion located intermediate said electrically insulative polymeric layer and said lower disposed surface of said electrically conductive deformable cushion layer and adhesively retained in electrical contact with said lower disposed surface, for applying electrical bias to said crystal rearward surface and for receiving said charge output;

a retainer mounted upon said crystal mount in spaced adjacency with said window portion for compressibly retaining said crystal against said upwardly disposed surface of said electrically conductive deformable layer; and a circuit assembly for applying said electrical bias through said contact assembly, for receiving and electrically treating said charge outputs and for applying electrical ground to said crystal forward surface.

2. The instrument of claim 1 in which said retainer is a thin, elastomeric retainer mounted in tension over said crystal forward surface.

3. The instrument of claim 2 in which said elastomeric retainer is a thin, electrically conductive elastomeric sheet electrically coupled with said circuit assembly and having an inwardly disposed surface in electrical ground supplying contact with said crystal forward surface.

4. The instrument of claim 3 in which said thin, elastomeric retainer is an electrically conductive carbon filled rubber sheet.

5. The instrument of claim 1 in which said electrically insulative elastomeric layer is silicone rubber.

6. The instrument of claim 1 in which said electrically conductive deformable cushion layer is a carbon-filled non-woven polytetrafluoroethylene cloth.

7. A laparoscopic instrument for detecting tissue at which a radiation emitting locator is concentrated, comprising:

a hand grippable base portion;

a rigid elongate accessing tube dimensioned for slidable movement through a laparoscopic cannula, fixed to said base portion, extending along a centrally disposed axis toward a tip a length effective for accessing said tissue, having a detector support region including a substantially planar window through which said radiation may be transmitted extending rearwardly from said tip toward said base portion;

a cadmium telluride crystal having a periphery exhibiting a lengthwise extent along said axis greater than its widthwise extent, having a rearward surface and a side looking forward surface facing outwardly from said axis and positioned in closely spaced adjacency with said window, said longitudinal dimension and said widthwise extent providing an area of said forward surface effective to respond to radiation transmitted through said window to derive outputs having peak levels when said crystal forward surface is located substantially centrally with respect to said concentrated locator;

a crystal mount formed of radiation attenuating material positioned within said detector support region having a receiving cavity for receiving said crystal and locating said forward surface in closely spaced, substantially parallel side looking adjacency with said window, said cavity having an interior surface with a periphery corresponding with said crystal periphery and limiting the response of said crystal only to radiation transmitted through said window;

an electrically conductive contact assembly for applying electrical bias to said crystal rearward surface and for conveying said output;

a grounding assembly for applying electrical ground to said crystal forward surface; and a signal treatment and control circuit for providing said electrical bias and ground for receiving and electrically treating said outputs.

8. The laparoscopic instrument of claim 7 including:

an electrically insulative elastomeric polymeric layer positioned over said receiving cavity interior surface; and an electrically conductive deformable cushion layer with an upwardly disposed surface and having a lower disposed surface located in abutment with said electrically insulative elastomeric, polymeric layer and said electrically conductive contact assembly, said upwardly disposed surface being in freely abutting contact with said crystal rearward surface and conveying said electrical bias thereto, and said electrically conductive deformable cushion layer lower disposed surface being adhered to said contact assembly and said electrically insulative elastomeric polymeric layer with an elastomeric adhesive.

9. The laparoscopic instrument of claim 8 including a thin, elastomeric retainer mounted in tension over said crystal forward surface for compressibly retaining said crystal against said upwardly disposed surface of said electrically conductive deformable cushion layer.

10. The laparoscopic instrument of claim 7 in which said crystal forward surface is spaced less than about 2 mm from said window.

11. A laparoscopic instrument for locating tissue from which locator based radiation is emitted, comprising:

a hand grippable base portion;

a rigid elongate accessing tube fixed to said base portion, dimensioned for slideable movement through a laparoscopic cannula and extending along a central axis toward a tip a length effective for accessing said tissue, having a passageway extending therethrough, and a detector support portion, including a side looking flat window through which radiation may be transmitted, extending inwardly in generally parallel relationship with said axis from said tip toward said base portion;

a crystal, having a periphery with a lengthwise extent along said axis greater than its widthwise extent, having a rearward surface and a forward surface, said lengthwise extent and said widthwise extent providing an area of said forward surface effective to respond to radiation transmitted through said window to derive charge categorized outputs having peak levels when said crystal forward surface is substantially centered with respect to said tissue from which locator based radiation is emitted;

a crystal mount, formed of material attenuating said radiation, having a crystal receiving portion positioned at said detector support portion, said crystal receiving portion having a periphery corresponding with said crystal periphery for supporting said crystal and locating said forward surface in close adjacency with said window, said receiving portion limiting the response of said crystal to radiation transmitted through said window and of tenting said lengthwise extent in substantially side looking parallel relationship with said axis;

an electrically conductive contact assembly for applying an electrical bias to said crystal rearward surface and for conveying said charge categorized outputs;

a first pre-amplification stage mounted within said accessing tube in adjacency with said crystal, having an input for receiving said conveyed charge categorized outputs and deriving amplified outputs, said first preamplification stage effecting a filtering of said electrical bias and an integration of said charge categorized outputs;

an electrical transmission assembly having one end coupled with said first pre-amplification stage for receiving said amplified outputs and applying said bias and which extends along said passageway to an opposite end region at said base portion; and a signal treatment and control circuit connectible with said electrical transmission assembly opposite end for providing said electrical bias and for receiving and electrically treating said amplified outputs to provide output signals, said signal treatment and control circuit including a second preamplification stage positioned in the vicinity of said base and coupled with said transmission assembly opposite end for effecting supplementary amplification of said amplified outputs.

12. The laparoscopic instrument of claim 11 in which said window has an inwardly disposed surface located in closely spaced adjacency with said crystal forward surface so as to permit a positioning of said forward surface in close proximity with said tissue to enhance the detection of said emitted radiation.

13. The laparoscopic instrument of claim 11 in which:

said crystal is formed of cadmium telluride;

said crystal mount is formed of a gamma radiation attenuating material;

said receiving portion of said crystal mount includes a cavity having an interior surface, an electrically insulative polymeric layer positioned over said interior surface, an electrically conductive deformable cushion layer with an upwardly disposed surface and having a lower disposed surface located in abutment with said electrically insulative polymeric layer and adhered thereto with an elastomeric adhesive;

said electrically conductive contact assembly having a forward portion located intermediate said electrically insulative polymeric layer and said lower disposed surface of said electrically conductive deformable cushion layer and adhesively retained in electrical contact with said lower disposed surface by said elastomeric adhesive;

said crystal rearward surface is located in abutting relationship upon said electrically conductive deformable cushion layer upwardly disposed surface; and including a thin, elastomeric retainer mounted in tension over said crystal forward surface for compressibly retaining said crystal against said upwardly disposed surface of said electrically conductive deformable cushion layer.

14. The laparoscopic instrument of claim 13 in which said elastomeric retainer is a thin electrically conductive elastomeric sheet configured for asserting electrical ground at said crystal forward surface.

15. A laparoscopic instrument for detecting tissue at which locator based radiation is emitted, comprising:

a hand grippable base portion;

a rigid elongate accessing tube dimensioned for slidable movement through a laparoscopic cannula, fixed to said base portion extending along an axis to a tip a length effective for accessing said tissue, having a detector support region including a substantially planar side looking window with a substantially flat outwardly disposed window surface through which radiation may be transmitted extending inwardly from said tip toward said base portion;

a crystal mount formed of a polymeric material selected for attenuating Beta radiation without propagation of X-rays, having a crystal receiving portion positioned at said detector support region to locate said receiving portion in adjacency with said window;

a crystal, formed to respond to Beta radiation having a periphery with a lengthwise extent greater than its widthwise extent, having a rearward surface supported upon said crystal receiving portion to position a forward surface thereof in substantially side looking parallel relationship with said axis and in closely spaced adjacency with said window and responsive to said radiation transmitted through said window to derive a charge categorized output;

an electrically conductive contact assembly for applying an electrical bias to said crystal rearward surface and for conveying said charge categorized output;

at least one pre-amplification stage mounted within said accessing tube in adjacency with said crystal, having an input for receiving said conveyed charge categorized output and deriving an amplified output;

an electrical transmission assembly having one end coupled with said pre-amplification stage for receiving said amplified output and applying said bias and which extends along said passageway to an opposite end region at said base portion; and a signal treatment and control circuit connectable with said electrical transmission assembly opposite end for providing said electrical bias and for receiving and electrically treating said amplified output to provide output signals.

16. The laparoscopic instrument of claim 15 in which said window is thin, flat material substantially transmissive of Beta radiation located in close adjacency with said crystal forward surface so as to permit a positioning of said forward surface in close proximity with said tissue to enhance the detection of said emitted radiation.

17. An instrument for detecting and locating sources of radiation emission comprising:

a cylindrical housing with an internally disposed chamber extending to a window region through which said radiation emission is transmissible:

a crystal mount positioned with said chamber and having a crystal receiving cavity with an interior surface and located in spaced adjacency with said window region;

an electrically insulative polymeric layer positioned over said receiving cavity interior surface;

an electrically conductive deformable cushion layer with an upwardly disposed surface, said layer having a lower disposed surface which is located in abutment with said electrically insulative layer and adhered thereto with an adhesive:

a radiation responsive crystal having a rearward surface freely abuttably positioned upon said upwardly disposed surface of said electrically conductive, deformable cushion layer, and having an oppositely disposed forward surface located in closely spaced adjacency with said window portion and responsive to said radiation transmitted therethrough to derive a charge output;

an electrically conductive contact assembly having a forward portion located intermediate said electrically insulative polymeric layer and said lower disposed surface of said electrically conductive deformable cushion layer and adhesively retained in electrical contact with said lower disposed surface, for applying electrical bias to said crystal rearward surface and for receiving said charge output;

a retainer including a thin, electrically conductive rubber sheet electrically coupled with said contact assembly and in ground supplying contact with said crystal forward surface mounted upon said crystal mount in spaced adjacency with said window portion, said sheet compressibly retaining said crystal against said upwardly disposed surface of said electrically conductive deformable layer; and a circuit for applying said electrical bias through said contact assembly and for receiving and electrically treating said charge output.

18. A laparoscopic instrument extensible through a cannula having a port of predetermined diameter for insertion within a body region for detecting tissue at which a radiation emitting locator is positioned, comprising:

a hand grippable base portion;

an elongate accessing tube dimensioned having a diameter less than said predetermined diameter for slidable movement through said port, fixed to said base portion, extending along an axis to a tip a length effective for accessing said tissue, having a detector support region including a substantially planar window through which said radiation may be transmitted extending inwardly from said tip;

a crystal mount formed of radiation attenuating material positioned within said detector support region having a receiving cavity with an interior surface, said cavity being located in spaced adjacency with said window;

a cadmium telluride crystal having a rearward surface mounted within said receiving cavity and having a forward surface positioned in spaced adjacency with said window and responsive to radiation transmitted therethrough generally transversely to said axis to derive an output;

an electrically conductive contact assembly for applying electrical bias to said crystal rearward surface and for conveying said output;

an electrically insulative polymeric layer positioned over said receiving cavity interior surface;

an electrically conductive deformable cushion layer with an upwardly disposed surface and having a lower disposed surface located in abutment with said electrically insulative layer and said electrically conductive contact assembly, said lower disposed surface being adhered to said contact assembly and said electrically insulative polymeric layer with an elastomeric adhesive, said upwardly disposed surface being in freely abutting contact with said crystal rearward surface and conveying said electrical bias thereto;

a grounding assembly comprising a thin conductive elastomeric sheet mounted in tension over said crystal forward surface and in electrical contact therewith for compressibly retaining said crystal against said upwardly disposed surface of said electrically conductive deformable cushion layer; and a signal treatment and control circuit for providing said electrical bias and ground and for receiving and electrically treating said output.

19. A laparoscopic instrument extensible through a cannula having a port of predetermined diameter for insertion within a body region for locating tissue from which locator based radiation is emitted, comprising:

a hand grippable base portion;

an elongate accessing tube fixed to said base portion, dimensioned having a diameter less than said predetermined diameter, for slidable movement through said port, extending along a central axis to a tip a length effective for accessing said tissue, having a passageway extending therethrough, and a detector support portion, including a window through which said radiation may be transmitted, extending inwardly from said tip;

a crystal mount formed of gamma radiation attenuating material having a crystal receiving portion positioned at said detector support portion to locate said receiving portion in adjacency with said window, said receiving portion including a cavity having an interior surface, an electrically insulative polymeric layer positioned over said interior surface, an electrically conductive deformable cushion layer with an upwardly disposed surface and having a lower disposed surface located in abutment with said electrically insulative polymeric layer and adhered thereto with an elastomeric adhesive;

a crystal, having a rearward surface located in abutting relationship upon said electrically conductive deformable cushion layer to position a forward surface of said crystal in closely spaced adjacency with said window and responsive to said radiation transmitted therethrough to derive a charge categorized output;

an electrically conductive contact assembly for applying an electrical bias to said crystal rearward surface and for conveying said charge categorized output, having a forward portion located intermediate said electrically insulative polymeric layer and said lower disposed surface of said electrically conductive deformable cushion layer and adhesively retained in electrical contact with said lower disposed surface by said elastomeric adhesive;

at least one pre-amplification stage mounted within said accessing tube in adjacency with said crystal, having an input for receiving said conveyed charge categorized output and deriving an amplified output;

an electrical transmission assembly having one end coupled with said pre-amplification stage for receiving said amplified output and applying said bias and which extends along said passageway to an opposite end region at said base portion;

a signal treatment and control circuit connectable with said electrical transmission assembly opposite end for providing said electrical bias and for receiving and electrically treating said amplified output to provide output signals; and a thin electrically conductive elastomeric sheet mounted in tension over said crystal forward surface and supplying electrical ground thereto.

20. A laparoscopic instrument for detecting tissue at which locator based radiation is emitted, comprising:

a hand grippable base portion;

a rigid elongate accessing tube fixed to said base portion, dimensioned for slideable movement through a laparoscopic cannula, extending along a central axis to a tip a length effective for accessing said tissue, having a passageway extending therethrough, and a detector support portion, including a flat side looking window through which said radiation may be transmitted, extending inwardly from said tip toward said base portion;

a crystal mount having a crystal receiving portion positioned at said detector support portion to locate said receiving portion in adjacency with said window;

a crystal, having a rectangularly shaped periphery and a lengthwise extent greater than its widthwise extent, having a rearward surface supported upon said crystal receiving portion to position a side looking forward surface thereof in closely spaced adjacency with said window and responsive to said radiation transmitted therethrough generally transversely to said axis to derive a charge categorized output;

an electrically conductive contact assembly for applying an electrical bias to said crystal rearward surface and for conveying said charge categorized output;

a first pre-amplification stage mounted within said accessing tube in adjacency with said crystal, having an input for receiving said conveyed charge categorized output and deriving an amplified output, said first preamplification stage effecting a filtering of said electrical bias and an integration of said charge categorized output;

electrical transmission assembly having one end coupled with said first pre-amplification stage for receiving said amplified output and applying said bias and which extends along said passageway to an opposite end region at said base portion; and a signal treatment and control circuit connectable with said electrical transmission assembly opposite end for providing said electrical bias and for receiving and electrically treating said amplified output to provide output signals, said signal treatment and control circuit including a second preamplification stage mounted within said hand grippable base portion and coupled with said transmission assembly opposite end for effecting supplementary amplification of said amplified output.

21. An instrument for detecting and locating sources of radiation emission, comprising:

a rigid cylindrical housing with an internally disposed chamber having a given diameter extending along a longitudinal axis to a tip, having a window region extending rearwardly from said tip with a flat, outwardly disposed side looking window surface through which said radiation emission is transmissible;

a crystal mount positioned within said chamber and having a crystal receiving cavity with an interior surface and a rectangular periphery, said mount being formed of material attenuating gamma radiation and located in spaced adjacency with said window region;

an electrically insulative elastomeric polymeric layer positioned over said receiving cavity interior surface;

an electrically conductive deformable cushion layer with an upwardly disposed surface, said layer having a lower disposed surface which is located in abutment with said electrically insulative layer and adhered thereto with an elastomeric adhesive;

a radiation responsive crystal having a rectangularly shaped periphery with a longitudinal dimension along said axis and a widthwise extent less than said longitudinal dimension, having a rearward surface freely abuttably positioned upon said upwardly disposed surface of said electrically conductive, deformable cushion layer, and having an oppositely disposed side looking forward surface spaced less than about 2 mm from said window region outwardly disposed window surface and responsive to said radiation transmitted through said window region to derive a charge output;

an electrically conductive contact assembly having a forward portion located intermediate said electrically insulative polymeric layer and said lower disposed surface of said electrically conductive deformable cushion layer and adhesively retained in electrical contact with said lower disposed surface, for applying electrical bias to said crystal rearward surface and for receiving said charge output;

a thin, electrically conductive elastomeric sheet mounted in tension over said crystal forward surface and in spaced adjacency with said window portion for compressibly retaining said crystal against said upwardly disposed surface of said electrically conductive deformable layer, and having an inwardly disposed surface in electrical ground supplying contact with said crystal forward surface; and a circuit assembly for applying said electrical bias through said contact assembly, for receiving and electrically treating said charge output, for applying electrical ground to said crystal forward surface, and electrically coupled with said elastomeric sheet.

* * * * *